(12) United States Patent
Iketani

(10) Patent No.: US 11,937,767 B2
(45) Date of Patent: Mar. 26, 2024

(54) ENDOSCOPE

(71) Applicant: HOYA CORPORATION, Tokyo (JP)

(72) Inventor: Kohei Iketani, Saitama (JP)

(73) Assignee: HOYA CORPORATION, Tokyo (JP)

( * ) Notice: Subject to any disclaimer, the term of this patent is extended or adjusted under 35 U.S.C. 154(b) by 441 days.

(21) Appl. No.: 17/297,808

(22) PCT Filed: Jul. 7, 2020

(86) PCT No.: PCT/JP2020/026525
§ 371 (c)(1),
(2) Date: May 27, 2021

(87) PCT Pub. No.: WO2021/010225
PCT Pub. Date: Jan. 21, 2021

(65) Prior Publication Data
US 2021/0393109 A1    Dec. 23, 2021

(30) Foreign Application Priority Data

Jul. 18, 2019 (JP) ................................ 2019-133163

(51) Int. Cl.
| | | |
|---|---|---|
| A61B 1/00 | (2006.01) |
| A61B 1/045 | (2006.01) |
| A61B 1/06 | (2006.01) |
| G06T 7/00 | (2017.01) |

(52) U.S. Cl.
CPC .... *A61B 1/00006* (2013.01); *A61B 1/000094* (2022.02); *A61B 1/000095* (2022.02);
(Continued)

(58) Field of Classification Search
CPC .......... A61B 1/00009; A61B 1/000094; A61B 1/000095; A61B 1/000096; G06T 7/0012;
(Continued)

(56) References Cited

U.S. PATENT DOCUMENTS

2015/0077529 A1    3/2015 Hatta et al.
2017/0256055 A1*   9/2017 Teramura .............. G06T 7/0012
(Continued)

FOREIGN PATENT DOCUMENTS

JP    11-104072      4/1999
JP    2003265408 A * 9/2003 ......... A61B 1/00009
(Continued)

OTHER PUBLICATIONS

Official Communication issued in International Bureau of WIPO Patent Application No. PCT/JP2020/026525, dated Sep. 15, 2020, along with an English translation thereof.
(Continued)

*Primary Examiner* — Timothy J Neal
(74) *Attorney, Agent, or Firm* — GREENBLUM & BERNSTEIN, P.L.C.

(57) ABSTRACT

A computer program or the like having high ability of detecting a lesion is provided. A computer program causes a computer to execute processing of: acquiring an image captured by an endoscope; inputting the image captured by the endoscope to a first recognizer that recognizes a lesion section on the basis of the image and a second recognizer that recognizes the lesion section with higher recognition accuracy than the first recognizer on the basis of the image; acquiring provisional information including a recognition result recognized by the first recognizer; outputting an image including the acquired provisional information; acquiring confirmation information for the provisional information including a recognition result recognized by the second recognizer; and outputting an image including the acquired confirmation information.

7 Claims, 14 Drawing Sheets

(52) U.S. Cl.
CPC ...... *A61B 1/000096* (2022.02); *A61B 1/0004* (2022.02); *A61B 1/045* (2013.01); *A61B 1/0655* (2022.02); *A61B 1/0661* (2013.01); *G06T 5/70* (2024.01); *G06T 7/0012* (2013.01); *G06T 2207/10068* (2013.01); *G06T 2207/30096* (2013.01)

(58) Field of Classification Search
CPC . G06T 2207/10068; G06T 2207/10024; G06T 2207/30096
See application file for complete search history.

(56) References Cited

U.S. PATENT DOCUMENTS

2019/0034800 A1 1/2019 Shiratani
2020/0193236 A1 6/2020 Oosake
2020/0305698 A1* 10/2020 Oosake .............. G02B 23/2484

FOREIGN PATENT DOCUMENTS

| JP | 2011-087793 | 5/2011 |
| JP | 2011087793 A * | 5/2011 |
| JP | 2013-258627 | 12/2013 |
| JP | 2017-153763 | 9/2017 |
| JP | 2017-213058 | 12/2017 |
| WO | 2017/175282 | 10/2017 |
| WO | 2019/054045 | 3/2019 |

OTHER PUBLICATIONS

Jul. 12, 2022 Japanese Office Action in corresponding Japanese Patent Application No. 2021-532990 and English translation thereof.

* cited by examiner

FIG. 6
A
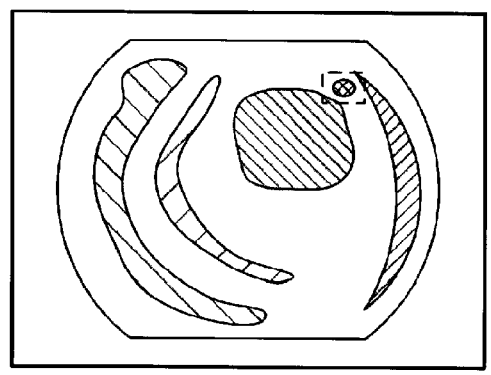
B
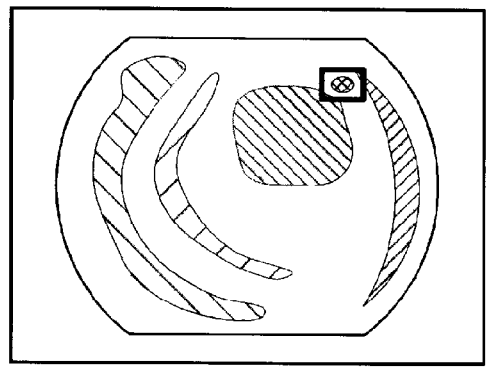
C
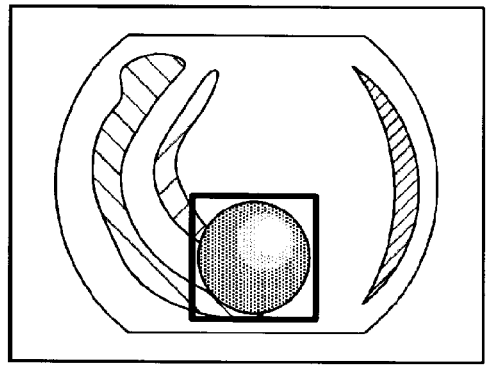

FIG. 8
A
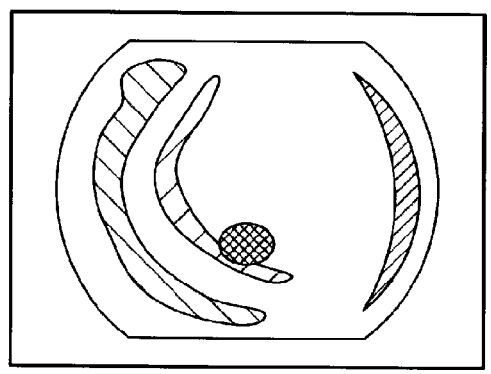
B
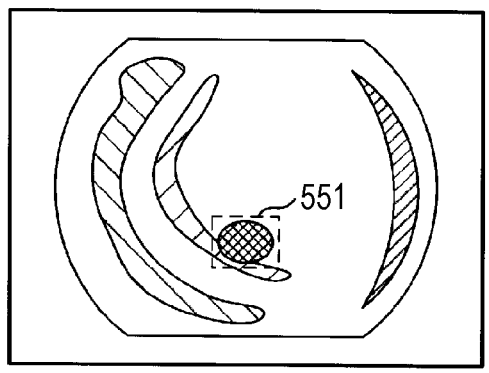
C
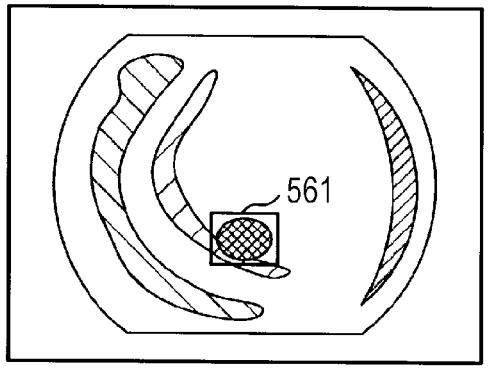
D
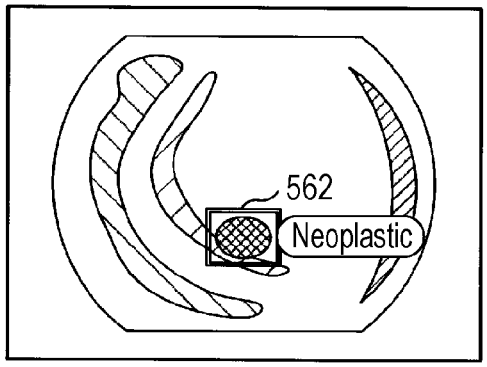

ENDOSCOPE

TECHNICAL FIELD

The present technology relates to a computer program, an information processing method, and an endoscope processor.

BACKGROUND ART

Computer-aided diagnostic technology has been developed which automatically detects a lesion section using a learning model from medical images such as endoscope images. A method of generating a learning model by supervised machine learning using training data with a correct answer label is known.

A learning method is proposed which combines a first learning using an image group taken by a normal endoscope as the training data and a second learning using an image group taken by a capsule endoscope as the training data (Patent Literature 1).

CITATION LIST

Patent Literature

Patent Literature 1: WO 2017/175282 A

SUMMARY OF INVENTION

Technical Problem

However, the method of Patent Literature 1 has a problem that the ability to detect a lesion is not sufficient.

An object of the present disclosure is to provide a computer program or the like having a high ability to detect a lesion.

Solution to Problem

A computer program according to an aspect of the present disclosure causes a computer to execute processing of: acquiring an image captured by an endoscope; inputting the image captured by the endoscope to a first recognizer that recognizes a lesion section on the basis of the image and a second recognizer that recognizes the lesion section with higher recognition accuracy than the first recognizer on the basis of the image; acquiring provisional information including a recognition result recognized by the first recognizer; outputting an image including the acquired provisional information; acquiring confirmation information for the provisional information including a recognition result recognized by the second recognizer; and outputting an image including the acquired confirmation information.

Advantageous Effects of Invention

According to the present disclosure, it is possible to provide a computer program or the like having high ability to detect a lesion.

BRIEF DESCRIPTION OF DRAWINGS

FIG. 6 is an explanatory diagram for explaining adjustment of light quantity information.

FIG. 8 is a view illustrating a screen example displayed on a display device.

DESCRIPTION OF EMBODIMENTS

Hereinafter, the present invention will be specifically described with reference to the drawings illustrating embodiments of the invention.

First Embodiment

Figure 1:
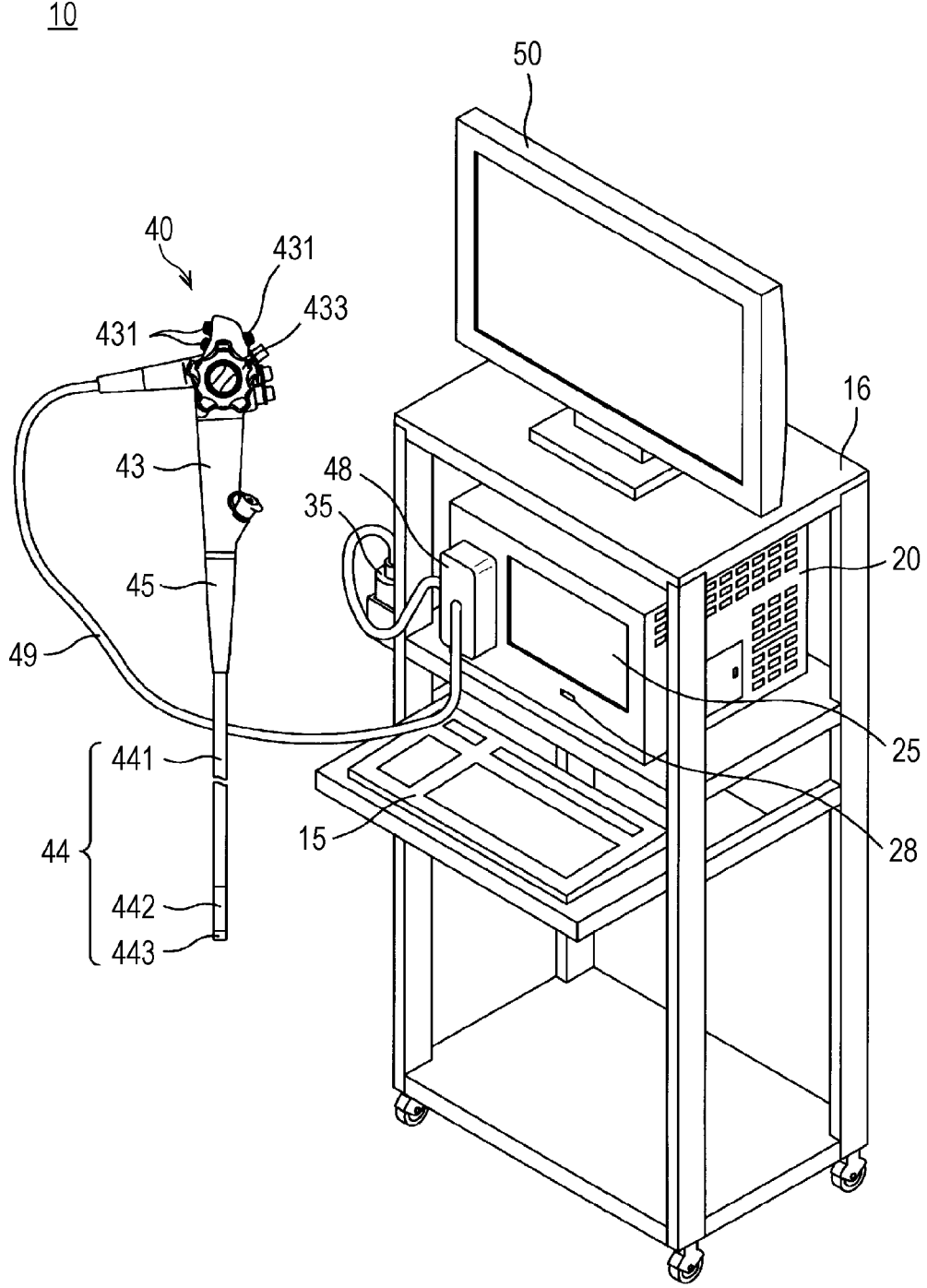
FIG. 1 is an explanatory diagram illustrating an appearance of a diagnostic support system.

FIG. 1 is an explanatory diagram illustrating an appearance of a diagnostic support system 10. The diagnostic support system 10 includes an endoscope processor 20, an endoscope 40, and a display device 50. The display device 50 is, for example, a liquid crystal display device or an organic electro luminescence (EL) display device.

The display device 50 is installed on the upper stage of a storage shelf 16 with casters. The endoscope processor 20 is housed in the middle stage of the storage shelf 16. The storage shelf 16 is arranged in the vicinity of an endoscopic examination bed (not illustrated). The storage shelf 16 includes a pull-out shelf on which a keyboard 15 connected to the endoscope processor 20 is mounted.

The endoscope processor 20 has a substantially rectangular parallelepiped shape and is provided with a touch panel 25 on one surface. A reading unit 28 is arranged at the bottom of the touch panel 25. The reading unit 28 is a connection interface for reading and writing a portable recording medium such as a USB connector, a secure digital (SD) card slot, or a compact disc read only memory (CD-ROM) drive.

The endoscope 40 includes an insertion portion 44, an operation unit 43, a light guide flexible tube 49, and a scope connector 48. The operation unit 43 is provided with a control button 431. The insertion portion 44 is long, and has one end connected to the operation unit 43 via a bend preventing portion 45. The insertion portion 44 includes a soft portion 441, a bending portion 442, and a distal tip 443 in the order from the operation unit 43 side. The bending portion 442 is bent according to an operation of a bending knob 433.

The light guide flexible tube 49 is long, and has a first end connected to the operation unit 43 and a second end connected to the scope connector 48. The light guide flexible tube 49 is flexible. The scope connector 48 has a substantially rectangular parallelepiped shape. The scope connector 48 is provided with an air/water supply port 36 (see FIG. 2) for connecting an air/water supply tube.

Figure 2:
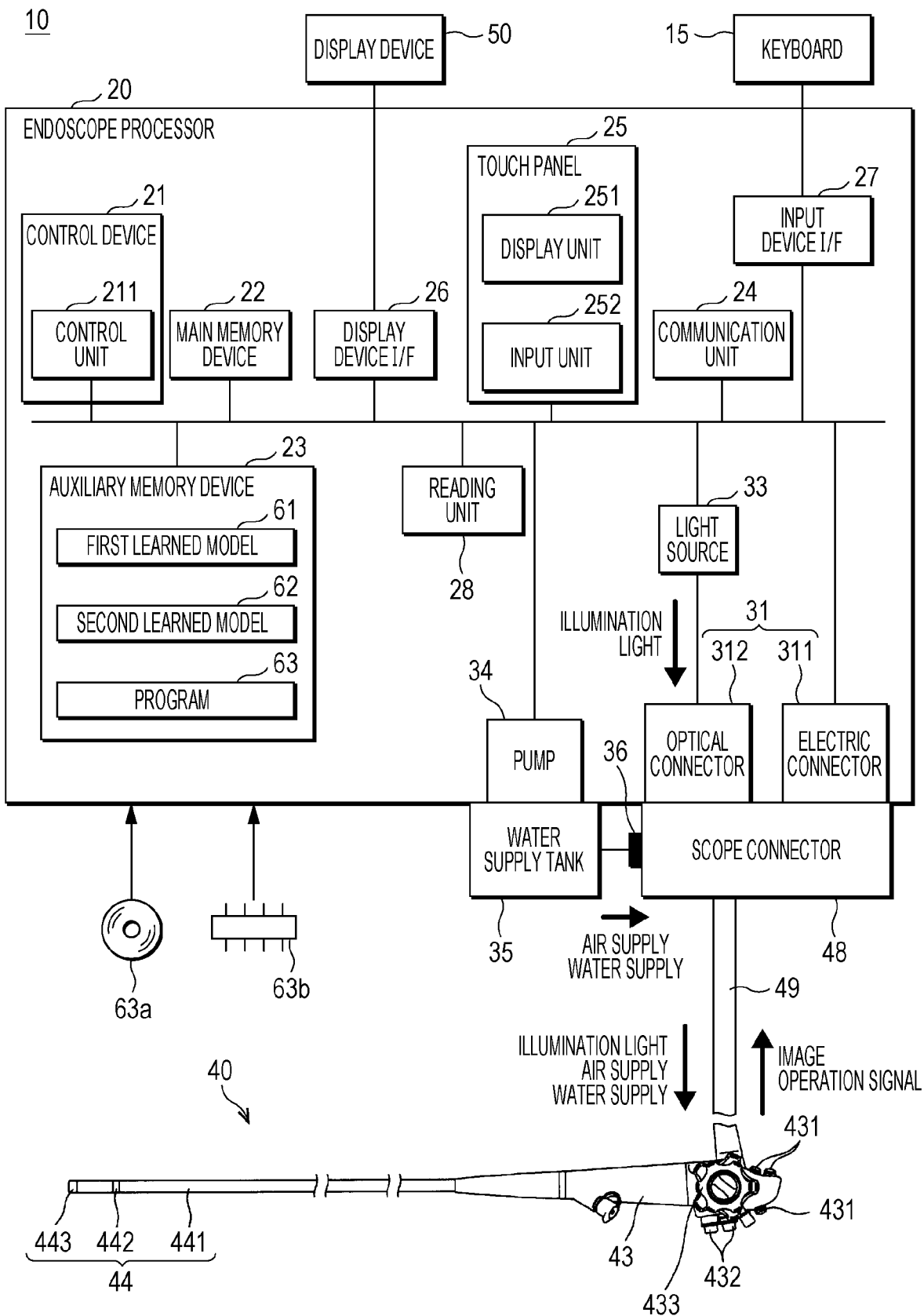
FIG. 2 is an explanatory diagram for explaining a configuration of the diagnostic support system.

FIG. 2 is an explanatory diagram for explaining a configuration of the diagnostic support system 10. As described above, the diagnostic support system 10 includes the endoscope processor 20, the endoscope 40, and the display device 50. In addition to the touch panel 25 and the reading unit 28, the endoscope processor 20 includes a control device 21, a main memory device 22, an auxiliary memory device 23, a communication unit 24, a display device interface (I/F) 26, and an input device I/F 27, an endoscope connector 31, a light source 33, a pump 34, and a bus. The endoscope connector 31 includes an electric connector 311 and an optical connector 312.

The control device 21 includes a control unit 211 and includes a circuit board or the like. Circuits such as a field programmable gate array (FPGA), an application specific integrated circuit (ASIC), and a central processing unit (CPU) which is an arithmetic control device for executing the program 63 of the present embodiment are mounted on the board. The control device 21 is connected to each hardware unit constituting the endoscope processor 20 via the bus.

The main memory device 22 is a memory device such as a static random access memory (SRAM), a dynamic random access memory (DRAM), and a flash memory. The main memory device 22 temporarily holds information necessary during the processing performed by the control unit 211 and a program being executed by the control unit 211.

The communication unit 24 is an interface for data communication between the endoscope processor 20 and the network. The touch panel 25 includes a display unit 251 such as a liquid crystal display panel, and an input unit 252 layered on the display unit 251.

The display device I/F 26 is an interface for connecting the endoscope processor 20 and the display device 50. The input device I/F 27 is an interface for connecting the endoscope processor 20 and an input device such as the keyboard 15.

The light source 33 is, for example, a high-luminance white light source such as a white LED. The light source 33 is connected to the bus via a driver (not illustrated). The on/off of the light source 33 and the change of brightness are controlled by the control unit 211. The illumination light emitted from the light source 33 is incident on the optical connector 312. The optical connector 312 engages with the scope connector 48 to supply illumination light to the endoscope 40.

The pump 34 generates pressure for the air supply/water supply function of the endoscope 40. The pump 34 is connected to the bus via a driver (not illustrated). The on/off and pressure change of the pump 34 are controlled by the control unit 211. The pump 34 is connected to the air/water supply port 36 provided in the scope connector 48 via a water supply tank 35.

The auxiliary memory device 23 is a memory device such as an SRAM, a flash memory, or a hard disk. The auxiliary memory device 23 stores a first learned model 61 that is a first recognizer, a second learned model 62 that is a second recognizer, a program 63 to be executed by the control unit 211, and various data necessary for executing the program 63. The first learned model 61, the second learned model 62, and the program 63 may be downloaded from an external device via a network such as the so-called Internet via the communication unit 24 and stored in the auxiliary memory device 23 by the control unit 211. The first learned model 61, the second learned model 62, and the program 63 may be read by the control unit 211 from a portable storage medium 63*a* via the reading unit 28 and stored in the auxiliary memory device 23. The first learned model 61, the second learned model 62, and the program 63 may be read from a semiconductor memory 63*b* by the control unit 211.

Figure 3:
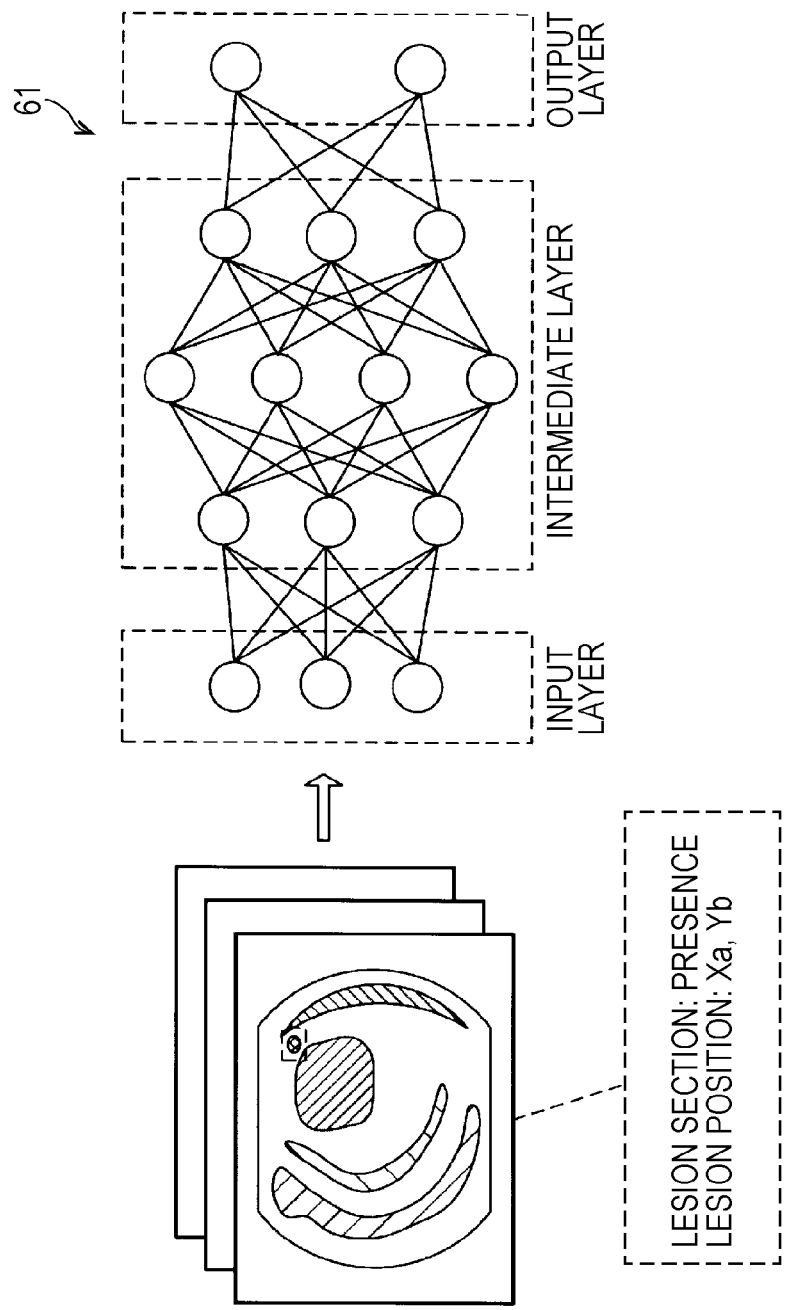
FIG. 3 is an explanatory diagram regarding generation processing of a first learned model in a first embodiment.

FIG. 3 is an explanatory diagram regarding generation processing of the first learned model 61 according to the first embodiment. The control unit 211 generates a learned model of machine learning including deep learning that inputs image information of the endoscope and outputs information indicating whether or not the lesion is included in the image. The control unit 211 performs machine learning of learning an image feature amount regarding a lesion of an inspection section in an image (original image 52) obtained by capturing the inspection section by the endoscope. The first learned model 61 is, for example, a neural network and is a convolution neural network (CNN). The first learned model 61 includes an input layer that receives an input of the image of the endoscope, an output layer that outputs information (identification result) indicating the presence or absence of the lesion, and an intermediate layer that extracts the image feature amount of the image of the endoscope.

The input layer has a plurality of neurons that accept an input of a pixel value of each pixel included in the image of the endoscope, and passes the input pixel value to the intermediate layer. The intermediate layer includes a plurality of neurons that extract the image feature amount of the image of the endoscope, and passes the extracted image feature amount to the output layer using various parameters. For example, if the first learned model 61 is a CNN, the intermediate layer has a configuration in which a convolution layer for convolving a pixel value of each pixel input from the input layer and a pooling layer for mapping the pixel values convolved in the convolution layer are alternately connected, and finally extracts the image feature amount while compressing the pixel information of an image region of an object. The output layer has one or a plurality of neurons that output an identification result indicating the presence or absence of the lesion, and outputs identification information indicating whether or not a lesion is included on the basis of the image feature amount output from the intermediate layer.

The control unit 211 learns various parameters in the intermediate layer using training data in which a plurality of images obtained by capturing the inspection section by the endoscope is associated with information regarding the lesion of the inspection section in each image. For example, as illustrated in FIG. 3, the training data is constructed as a data set in which the presence or absence of the lesion and a coordinate range of the image region corresponding to the lesion section are labeled with respect to the image of the endoscope. Note that the lesion may include a site that may be diagnosed as a lesion, that is, a lesion candidate. The control unit 211 performs learning using data obtained by collecting images and diagnosis results of a large number of inspections performed in the past. The data also includes an image in a state where it is diagnosed that there is no lesion. Note that in FIG. 3, the labeled image region is indicated by a broken rectangular frame. The image region corresponding to the lesion section may be extracted using, for example, a model visualization method such as Gradient-weighted Class Activation Mapping (Grad-CAM). The control unit 211 extracts a region strongly affecting the output from the output layer as the lesion section.

The control unit 211 inputs the image of the endoscope included in the training data to the input layer, performs arithmetic processing in the intermediate layer, and acquires an identification result indicating the presence or absence of the lesion from the output layer. For example, the control unit 211 acquires, as the identification result output from the output layer, an identification result of identifying an image region corresponding to the lesion section in addition to the presence or absence of the lesion in the image of the endoscope. The control unit 211 compares the identification result output from the output layer with information regarding a lesion labeled with the image in the training data, that is, a correct value, and optimizes various parameters used for calculation processing in the intermediate layer such that the output value from the output layer approaches the correct value. The parameter is, for example, a weight, a bias, or the like between the neurons. The method of optimizing various parameters is not particularly limited, but for example, the control unit 211 optimizes various parameters using an error back propagation method. The control unit 211 performs the above processing on each image included in the training data to generate the first learned model 61.

Figure 4:
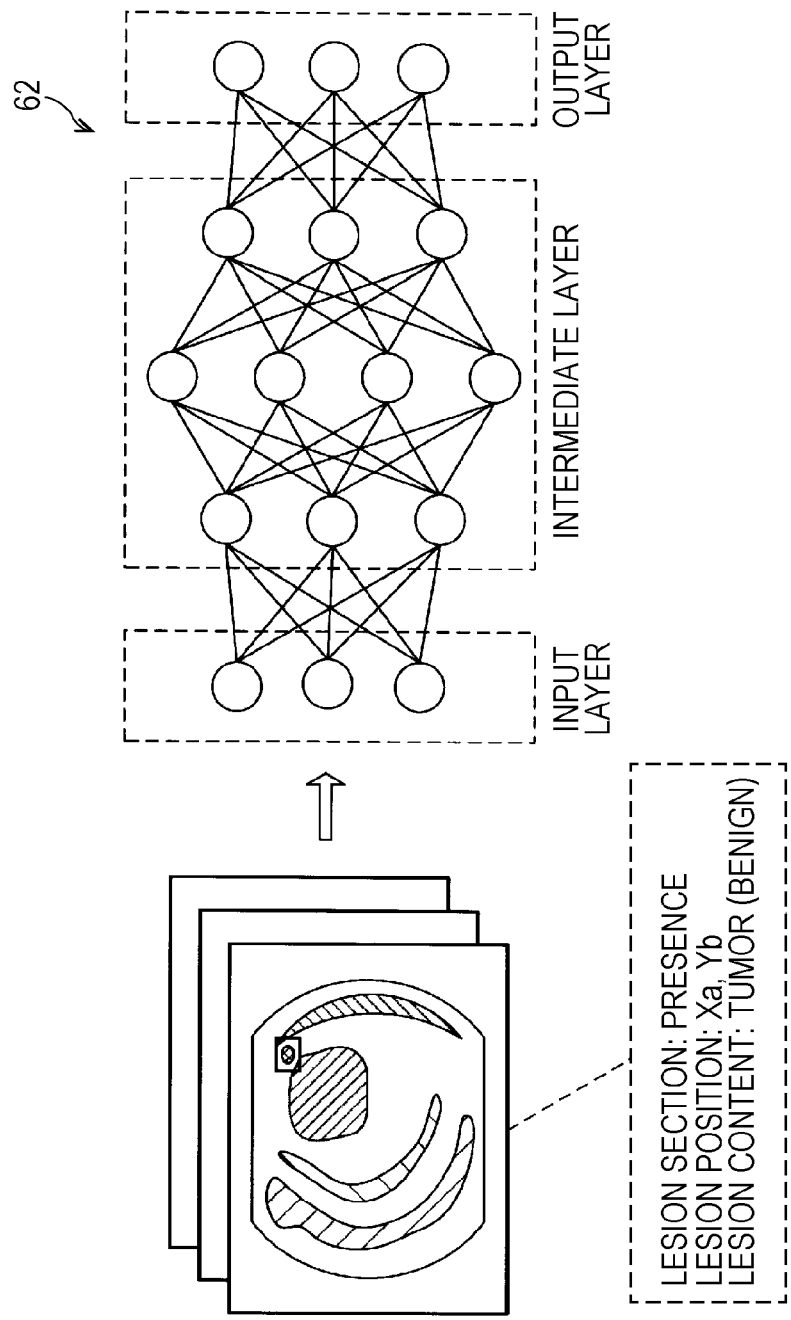
FIG. 4 is an explanatory diagram regarding generation processing of a second learned model.

FIG. 4 is an explanatory diagram regarding generation processing of a second learned model 62. The second learned model 62 inputs an image (processed image 54) of the endoscope, which is subjected to predetermined preprocessing to be described later and can be identified with high accuracy to the image (original image 52) of the endoscope input to the first learned model 61. The second learned model 62 outputs an estimation result indicating the presence or absence of the lesion in the image of the endoscope and the content of the lesion (tumor/benign, tumor/malignant, etc.). The control unit 211 generates a learned model of machine learning including deep learning that inputs the image information of the endoscope and outputs the information indicating the presence or absence and the content of the lesion in the image. The control unit 211 performs machine learning of learning an image feature amount regarding a lesion of an inspection section in an image (processed image 54) obtained by capturing the inspection section by the endoscope. The second learned model 62 is, for example, a neural network and is a CNN. The second learned model 62 includes an input layer that receives an input of the image of the endoscope, an output layer that outputs information (identification result) regarding a lesion, and an intermediate layer that extracts the image feature amount of the image of the endoscope.

The input layer has a plurality of neurons that accept an input of a pixel value of each pixel included in the image of the endoscope, and passes the input pixel value to the intermediate layer. The intermediate layer includes a plurality of neurons that extract the image feature amount of the image of the endoscope, and passes the extracted image feature amount to the output layer using various parameters. For example, if the second learned model 62 is a CNN, the intermediate layer has a configuration in which a convolution layer for convolving a pixel value of each pixel input from the input layer and a pooling layer for mapping the pixel values convolved in the convolution layer are alternately connected, and finally extracts the image feature amount while compressing the pixel information of an image region of an object. The output layer has one or a plurality of neurons that output an identification result indicating the information regarding the lesion, and outputs identification information indicating the presence or absence and the content of the lesion on the basis of the image feature amount output from the intermediate layer.

The control unit 211 learns various parameters in the intermediate layer using training data in which a plurality of images obtained by capturing the inspection section by the endoscope is associated with information regarding the lesion of the inspection section in each image. For example, as illustrated in FIG. 3, the training data is constructed as a data set in which the presence or absence of the lesion, a coordinate range of the image region corresponding to the lesion section, and the content of the lesion are labeled with respect to the image of the endoscope. The control unit 211 performs learning using data obtained by collecting images and diagnosis results of a large number of inspections performed in the past. The data also includes an image in a state where it is diagnosed that there is no lesion. Note that in FIG. 4, the labeled image region is indicated by a thick rectangular frame.

The control unit 211 inputs the image of the endoscope included in the training data to the input layer, performs arithmetic processing in the intermediate layer, and acquires an identification result indicating the presence or absence and the content of the lesion from the output layer. For example, the control unit 211 acquires, as the identification result output from the output layer, an identification result of identifying an image region corresponding to the lesion section and the content of the lesion, in addition to the presence or absence of the lesion in the image of the endoscope. The control unit 211 compares the identification result output from the output layer with information regarding a lesion labeled with the image in the training data, that is, a correct value, and optimizes various parameters used for calculation processing in the intermediate layer such that the output value from the output layer approaches the correct value. The parameter is, for example, a weight, a bias, or the like between the neurons. The method of optimizing various parameters is not particularly limited, but for example, the control unit 211 optimizes various parameters using an error back propagation method. The control unit 211 performs the above processing on each image included in the training data to generate the second learned model 62.

The second learned model 62 may be a learned model having the same configuration as the first learned model 61, and the second learned model 62 may be a learned model including an intermediate layer having a larger number of layers than the first learned model 61 and having improved image recognition accuracy. The second learned model 62 may have a longer processing time than the first learned model 61. For example, in the first learned model 61, grayscale image information is given to the input information, and in the second learned model 62, image information including red green blue (RGB) values is given to the input information.

Note that in the present embodiment, it has been described that the first learned model 61 and the second learned model 62 are CNNs, but the first learned model 61 and the second learned model 62 are not limited to the CNNs and neural networks other than the CNNs may be used. In addition, the first learned model 61 and the second learned model 62 may be learned models constructed by another learning algorithm such as a reinforcement learning model, a support vector machine, or a regression tree that does not use the neural network. The first learned model 61 and the second learned model 62 may be learned models constructed by an arbitrary object detection algorithm such as R-CNN, Faster R-CNN, Mask R-CNN, Single Shot Multibook Detector (SSD), or You Only Look Once (YOLO). In a case where a plurality of lesion sections are detected in the input image, each lesion section may be input to the first learned model 61 and the second learned model 62, and a recognition result may be output. Note that the first learned model 61 and the second learned model 62 may be generated by an external device and installed in the endoscope processor 20.

In addition, in the present embodiment, an example in which the learned model is applied to the first recognizer and the second recognizer has been described, but a method of recognizing the lesion by the image of the endoscope is not limited. For example, the first recognizer and the second recognizer may calculate the image feature amount of the image of the endoscope, and recognize the presence or absence or the content of the lesion included in the image of the endoscope by pattern matching or the like with a lesion image stored in advance.

Figure 5:
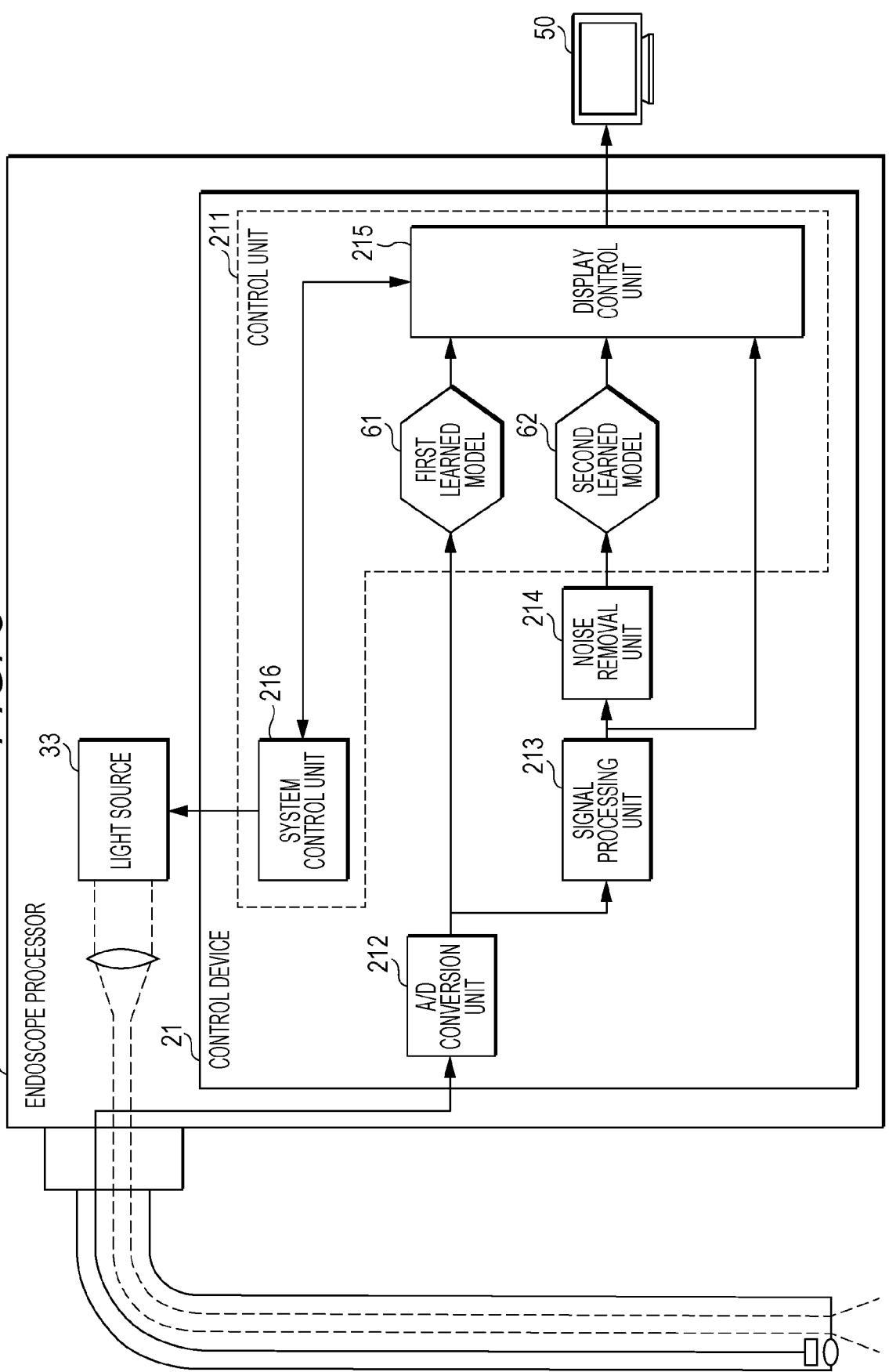
FIG. 5 is a functional block diagram illustrating a configuration of a control device.

FIG. 5 is a functional block diagram illustrating a configuration of the control device 21. The control device 21 includes a control unit 211, an A/D conversion unit 212, a signal processing unit 213, and a noise removal unit 214. The control unit 211 is an arithmetic control device that executes the program 63 of the present embodiment, and one or a plurality of CPUs, a multi-core CPU, or the like is used. In addition, the control unit 211 implements the functions of the display control unit 215 and the system control unit 216 by executing the program 63 stored in the auxiliary memory device 23. In FIG. 5, these sections are illustrated as functional units.

The A/D conversion unit 212 uses, for example, an A/D converter. The A/D conversion unit 212 converts an electric signal of a captured image 51 captured by an image sensor provided at a distal tip 443 of the endoscope 40 and transmitted to the endoscope processor 20 into digital data (RAW data). The captured image 51 is obtained as a moving image, and includes a still image of a plurality frames such as 60 frames per second, for example. Here, the RAW data refers to data obtained by A/D converting an analog signal obtained from the image sensor, and is data which is not subjected to other corrections. The A/D conversion unit 212 converts the captured image 51 into the original image 52 which is the RAW data. Note that the A/D conversion unit 212 may perform only signal processing that does not cause a time delay on the original image 52 which is the RAW data. The original image 52 converted by the A/D conversion unit 212 is input to the first learned model 61 and the signal processing unit 213.

The signal processing unit 213 is a signal processing circuit that performs various types of image processing such as gamma correction, contour enhancement, and enlargement/reduction of the original image 52 using ASIC or the like. The signal processing unit 213 performs processing of changing a bit number of the original image 52 as necessary, and performs image processing of converting the original image 52 having a 10-bit gradation converted by the A/D conversion unit 212 into an 8-bit gradation and changing the bit number to a bit number suitable for subsequent image processing, for example. The signal processing unit 213 generates an image (endoscope image 53) subjected to image processing for making it easy for the user to view the image, and inputs the image to the display control unit 215. In addition, the signal processing unit 213 inputs an image subjected to image processing for improving the lesion recognition accuracy to the noise removal unit 214.

The noise removal unit 214 is a so-called video memory, and includes a memory for holding images of immediately preceding and further immediately preceding frames of noise removal. The noise removal unit 214 performs image processing of removing noise from the image of the target frame on the basis of a difference from the images of the immediately preceding and further immediately preceding frames. The image (processed image 54) subjected to the image processing by the signal processing unit 213 and the noise removal unit 214 is input to the second learned model 62.

The control unit 211 functions as the first learned model 61 by executing the program 63 stored in the auxiliary memory device 23 or reading an entity file constituting the first learned model 61. The first learned model 61 outputs information regarding the presence or absence of the lesion to the display control unit 215 according to the original image 52.

The control unit 211 functions as the second learned model 62 by executing the program 63 stored in the auxiliary memory device 23 or reading an entity file constituting the second learned model 62. The second learned model 62 outputs information regarding the presence or absence and the content of the lesion to the display control unit 215 according to the processed image 54.

The display control unit 215 acquires provisional information based on the output information from the first learned model 61 and confirmation information based on the output information from the second learned model 62, and controls the display of a provisional information image 55 including the provisional information and a confirmation information image 56 including the confirmation information on the display device 50. Furthermore, the display control unit 215 acquires light quantity information regarding brightness of a captured region including the lesion section of the original image 52 on the basis of the output information from the first learned model 61. In a case where the captured image of the region including the lesion section is too bright or too dark, a recognition accuracy for the image in the learned model may decrease. Based on the output information from the first learned model 61, the display control unit 215 derives the light quantity information in which the brightness of the lesion section of the original image 52 is determined. The derived light quantity information is input to the system control unit 216.

The system control unit 216 reads a light quantity control information database (not illustrated) stored in advance, specifies appropriate light quantity control information based on the acquired light quantity information, and outputs the specified light quantity control information to the light source 33 of the endoscope processor 20 to control a light quantity of the light source 33. Since the light quantity of the light source 33 is reduced or increased as necessary under the control of the system control unit 216, the captured image 51 in which the brightness of the lesion section has been appropriately adjusted is obtained, and the processed image 54 in which the brightness and color of the lesion section have been adjusted is input to the second learned model 62.

FIG. 6 is an explanatory diagram for explaining adjustment of light quantity information. FIG. 6A illustrates an example of an image in a state where the lesion section is included on an inner side of the right. In general, an image is displayed such that a region on the front side of the image is brighter and a region on the inner side is darker. Therefore, in a case where the image is captured in a state where the lesion section is included on the inner side of the right, as illustrated in FIG. 6A, a region including the lesion section is displayed darkly, and there is a possibility that a highly accurate recognition result cannot be obtained by the second recognizer although identification can be performed by the first recognizer. In such a case, the control unit 211 acquires the light quantity information indicating that the brightness is low based on the image information, and specifies the light quantity control information based on the acquired light quantity information. Based on the specified light quantity control information, the control unit 211 outputs, for example, control information for increasing the light quantity to a predetermined value to the light source 33.

FIG. 6B illustrates an example of an image in which the lesion section is included on the inner side of the right after the adjustment based on the light quantity information is performed. When the light quantity of the light source 33 is increased as described above, an image in which a region including the lesion section is bright as illustrated in FIG. 6B is obtained. The recognizer can make a determination based on the image in which the brightness and color of the lesion section have been adjusted.

FIG. 6C illustrates an example of an image in a state where the lesion section is included on a front side. In the example illustrated in FIG. 6C, the lesion section is included on the front side, and halation due to excessive light quantity occurs in a portion of the inside of the lesion section. As illustrated in FIG. 6C, in a case where halation occurs in the image, the first recognizer can perform identification, but there is a possibility that a highly accurate recognition result cannot be obtained by the second recognizer. In such a case, the control unit 211 acquires the light quantity information indicating that the brightness is high based on the image information, and specifies the light quantity control information based on the acquired light quantity information. Based on the specified light quantity control information, the control unit 211 outputs, for example, control information for reducing the light quantity to a predetermined value to the light source 33. In this way, the brightness of the entire image in which the light quantity is appropriately adjusted decreases, and an image in which the halation does not occur in a region of interest can be obtained even in a case where the lesion section is on the front side.

Figure 7:
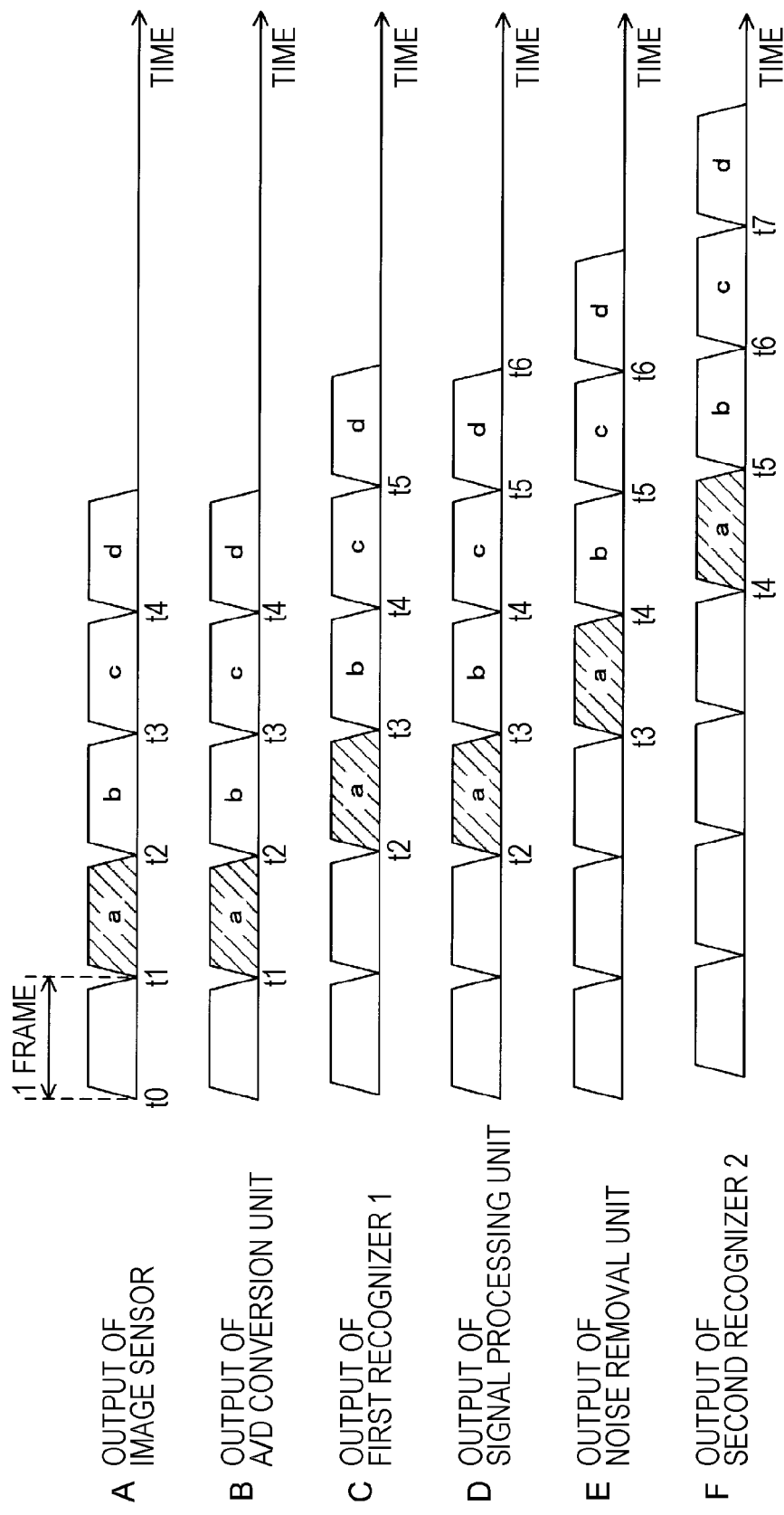
FIG. 7 is a time chart for schematically explaining an operation of the diagnostic support system.

FIG. 7 is a time chart for schematically explaining an operation of the diagnostic support system 10. A horizontal axis represents time. FIG. 7A illustrates a timing of outputting the captured image 51 by the image sensor 141. FIG. 7B illustrates a timing at which the original image 52 is output by the image processing of the A/D conversion unit 212. FIG. 7C illustrates timing at which the first recognizer (first learned model 61) outputs provisional information based on the original image 52. FIG. 7D illustrates a timing at which an image processed by the image processing of the signal processing unit 213 is output. FIG. 7E illustrates a timing at which the processed image 54 is output by the image processing of the noise removal unit 214. FIG. 7F illustrates timing at which the second recognizer (the second learned model 62) outputs confirmation information based on the processed image 54.

At time t1, the image sensor 141 outputs a frame "a" of the captured image 51. The A/D conversion unit 212 performs A/D conversion processing, and outputs the original image 52 of "a" at time t1. At time t2, the control unit 211 inputs the original image 52 to the first learned model 61 and outputs provisional information including a recognition result. The control unit 211 displays the provisional information image 55 on the display device 50 and outputs light quantity information. In addition, at time t2, the signal processing unit 213 performs image processing and outputs an image subjected to the image processing of "a". At time t3, the noise removal unit 214 performs image processing and outputs a processed image 54 of "a". At time t4, the control unit 211 inputs the processed image 54 to the second learned model 62 and outputs confirmation information including a recognition result. The control unit 211 displays the confirmation information image 56 on the display device 50. As a result, the processing of an image corresponding to one frame captured by the image sensor 141 is terminated. Similarly, at time t2, the image sensor 141 outputs a frame "b". Since the subsequent operations are the same, the description thereof will be omitted.

In the example illustrated in FIG. 7, the provisional information is output one frame later than the output of the image sensor 141, and the confirmation information is output two frames later than the output of the provisional information. Since the output from the first recognizer is obtained simultaneously with the output of the signal processing unit 213, the user can obtain the provisional information almost without feeling a delay. Since the output from the second recognizer is delayed by three frames from the output of the image sensor, if one frame period is set to, for example, 33 ms, the output is delayed by about 0.1 seconds, and thus the user may feel a slight delay.

Note that, in a case where the light quantity is adjusted in response to the output of the light quantity information at the time t2, the output of the confirmation information is obtained with a further delay. For example, in a case where the light quantity information is output and the light source is controlled at time t3 upon receiving the output information of the first learned model 61 of "a", a frame of "d" output at time t4 corresponds to a frame controlled to have an appropriate light quantity on the basis of "a". Therefore, the confirmation information after the light quantity adjustment is output six frames later than the output of the image sensor at time t7.

The function of the endoscope 40 connected to the endoscope processor 20 will be outlined. A fiber bundle, a cable bundle, an air supply tube, a water supply tube, and the like are inserted inside the scope connector 48, the light guide flexible tube 49, the operation unit 43, and the insertion portion 44. The illumination light emitted from the light source 33 is radiated from an illumination window provided at the distal tip 443 via the optical connector 312 and the fiber bundle.

The range illuminated by the illumination light is captured by an image sensor provided at the distal tip 443. The captured image 51 is transmitted from the image sensor to the endoscope processor 20 via the cable bundle and the electric connector 311.

The control unit 211 performs image processing on the captured image 51 to generate an endoscope image 53 that makes it easy for the user to visually find a lesion. The control unit 211 generates a provisional information image 55 including the provisional information based on the recognition result of the first learned model 61. The control unit 211 generates a confirmation information image 56 including the confirmation information based on the recognition result of the second learned model 62. The control unit 211 outputs the endoscope image 53, the provisional information image 55, and the confirmation information image 56 to the display device 50.

FIG. 8 is a view illustrating a screen example displayed on the display device 50. FIG. 8A illustrates an example of a display screen of the endoscope image 53. During the endoscopic examination, the endoscope image 53 is updated in real time. The user who operates the endoscope 40 operates the endoscope 40 while observing the endoscope image 53.

FIG. 8B illustrates an example of a display screen of the provisional information image 55. In the example of FIG. 8B, the provisional information image 55 is an image in which the provisional information is superimposed and displayed on the endoscope image 53. The provisional information is information based on the recognition result of the first learned model 61, and includes the recognition result of the presence or absence and the position of the lesion in the image region. The provisional information is displayed on the display device 50 in a form that can be recognized by the user. In the example of FIG. 8B, the provisional information is displayed by a provisional marker 551 indicated by a dashed bounding box including a region recognized as the lesion in the first learned model 61.

FIG. 8C illustrates an example of a display screen of a first example of the confirmation information image 56. In the example of FIG. 8C, the confirmation information image 56 is an image in which the confirmation information is superimposed and displayed on the endoscope image 53. The confirmation information is information based on the recognition result of the second learned model 62, and includes the recognition result of the content and position of the lesion in the image region. The confirmation information is displayed on the display device 50 in a form that can be recognized by the user. In the example of FIG. 8C, the confirmation information is displayed by a confirmation marker 561 indicated by a bold bounding box including a region recognized as the lesion in the second learned model 62. The confirmation information may be displayed including text or the like indicating the contents of the lesion.

FIG. 8D illustrates an example of a display screen of a second example of the confirmation information image 56. In the example of FIG. 8D, the confirmation information image 56 is an image in which the confirmation information is superimposed and displayed on the endoscope image 53. The confirmation information is displayed using a confirmation marker 562 indicated by a solid bounding box including a region recognized as a lesion (benign) in the second learned model 62 and a text ("Neoplastic" or the like) indicating the content of the recognition result. The bounding box is indicated by a double rectangular frame. As illustrated in FIG. 8D, in a region provisionally recognized as the lesion by the first recognizer, in a case where confirmation information including a recognition result such as no lesion or benign lesion is obtained by the second recognizer, the control unit 211 displays the confirmation information image 56 including information for deleting the provisional marker 551 or information for displaying the confirmation marker 562 indicating that the lesion section is benign, text, and the like.

The confirmation markers 561 and 562 are desirably displayed in a different color or shape according to the content (benign or malignant) of the lesion. For example, the confirmation information may be displayed with a marker indicated by green when the lesion section is benign, or by red when the lesion section is malignant, and the confirmation information may be displayed with a marker indicated by a circle when the lesion section is benign, or by a square when the lesion section is malignant. The confirmation information may be output by reading out a text by synthesized speech, or may be output using different music or the like corresponding to the content of the lesion, in addition to being displayed using the confirmation marker. In addition, in a case where the confirmation markers 561 and 562 indicating a plurality of lesion sections are included in the confirmation information image 56, for example, a beep sound, music, or the like in which a frequency, a tempo, an output frequency, or the like is changed according to the number of lesion sections may be output. In addition, a numerical value indicating the number of confirmation markers indicating the lesion sections may be displayed.

Figure 9:
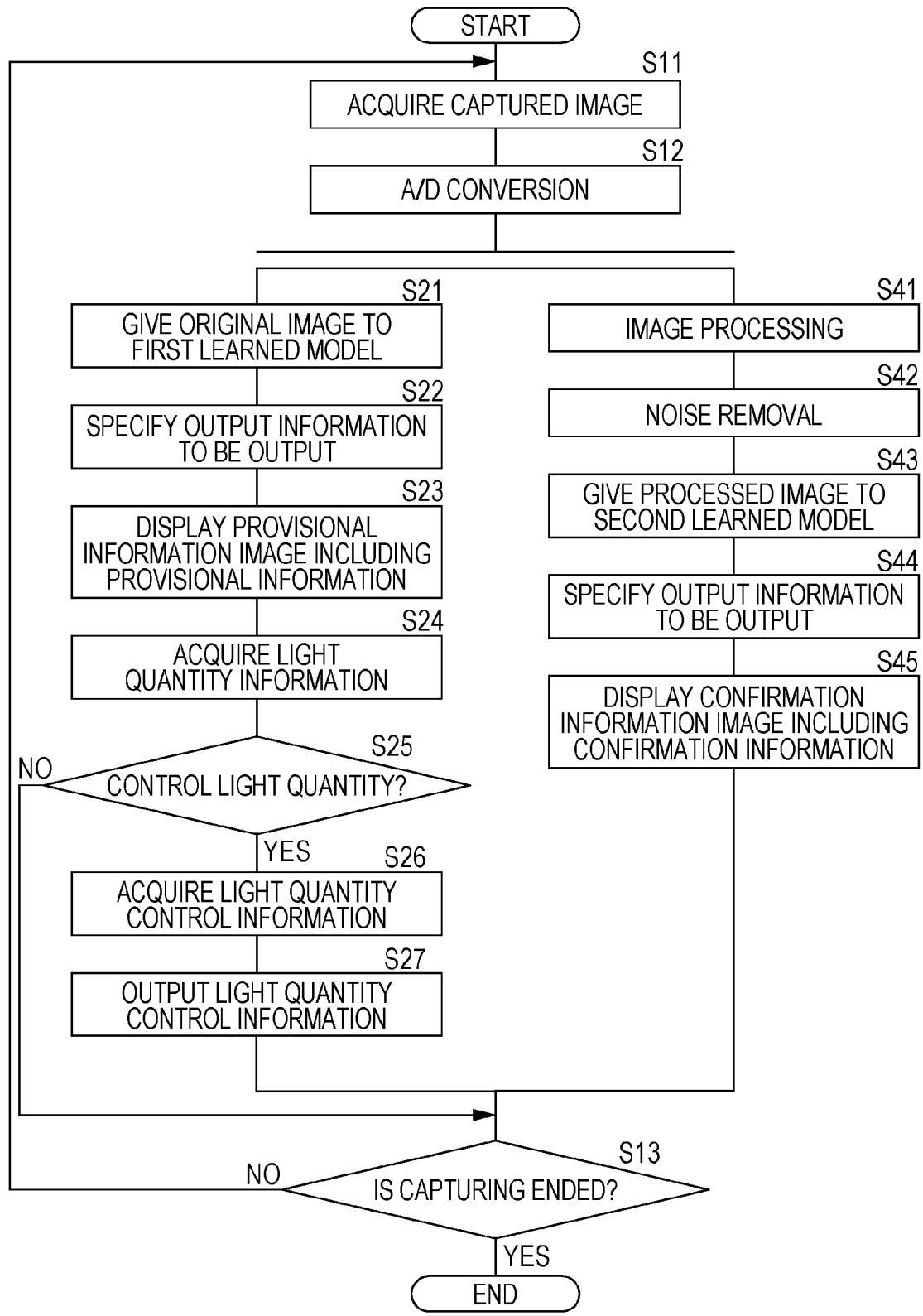
FIG. 9 is a flowchart illustrating an example of a processing procedure executed in the diagnostic support system.

FIG. 9 is a flowchart illustrating an example of a processing procedure executed by the diagnostic support system 10. The flowchart illustrated in FIG. 9 describes processing executed by the control unit 211, the A/D conversion unit 212, the signal processing unit 213, and the noise removal unit 214 of the endoscope processor 20. The control unit 211 executes the processing illustrated in FIG. 9 together with processing such as generation of the endoscope image 53 and control of the light source 33 and the image sensor arranged at the distal tip 443 of the endoscope 40.

The A/D conversion unit 212 acquires a captured image 51 from the endoscope 40 (step S11). The A/D conversion unit 212 A/D converts the acquired captured image 51 (step S12) to generate the original image 52. The control unit 211 gives the original image 52 to the first learned model 61 (step S21), and specifies output information to be output (step S22). The control unit 211 temporarily stores provisional information based on the specified output information in the auxiliary memory device 23. The control unit 211 generates the provisional information image 55 in which the provisional information is superimposed and displayed on the endoscope image 53, and displays the provisional information image 55 including the provisional information on the display device 50 (step S23). For example, a confirmation information image indicating a provisional marker at a lesion section is displayed.

The control unit 211 or the like generates a sub-process and performs the processing of step S41 in parallel with the processing of step S21 and subsequent steps. The signal processing unit 213 performs various types of image processing on the original image 52 (step S41). The noise removal unit 214 performs noise removal on the image subjected to the image processing (step S42), and generates the processed image 54.

The control unit 211 gives the processed image 54 to the second learned model 62 (step S43), and specifies output information to be output (step S44). The control unit 211 temporarily stores confirmation information based on the specified output information in the auxiliary memory device 23. The control unit 211 generates a confirmation information image 56 in which the confirmation information is superimposed and displayed on the endoscope image 53, and displays the confirmation information image 56 including the confirmation information on the display device 50 (step S45). For example, in a case where the provisional information of the first learned model 61 and the confirmation information of the second learned model 62 include the same recognition result for the lesion, the control unit 211 displays the confirmation information image 56 indicating the confirmation marker 561 instead of the provisional information image 55 including the lesion section indicated by the provisional marker 551. In addition, in a case where the provisional information of the first learned model 61 and the confirmation information of the second learned model 62 include different contents, the control unit 211 displays the confirmation information image 56 in which the provisional marker 551 displayed at the lesion section is deleted instead of the provisional information image 55 including the lesion section indicated by the provisional marker 551.

After the processing of step S23, the control unit 211 acquires light quantity information regarding brightness of the image of the captured region including the lesion section of the original image 52 (step S24). The control unit 211 determines whether or not to control the light quantity of the light source 33 on the basis of the light quantity information (step S25). For example, in a case where the brightness of the captured region including the lesion section of the original image 52 is within a range of a preset threshold value, it is determined that the light quantity control is unnecessary because the brightness of the lesion section is appropriate. If it is determined that that the light quantity control is unnecessary (step S25: NO), the control unit 211 skips the processing of the light quantity control and proceeds to step S13.

On the other hand, in a case where the brightness of the captured region including the lesion section of the original image 52 is equal to or higher than a preset threshold value or equal to or lower than a preset threshold value, it is determined that the light quantity control is necessary because the lesion section is too bright or too dark. If it is determined that the light quantity control is necessary (step S25: YES), the control unit 211 refers to a light quantity control information database stored in advance and acquires light quantity control information according to the light quantity information (step S26). The control unit 211 outputs the acquired light quantity control information to the light source 33 of the endoscope processor 20 (step S27). The light quantity of the light source 33 is controlled.

The control unit 211 determines whether or not the capturing has ended (step S13). If it is determined that the capturing has not been ended (step S13: NO), the control unit 211 returns the processing to step S11 and acquires a new captured image. If it is determined that the capturing has been ended (step S13: YES), the control unit 211 or the like ends a series of processing. Note that the control unit 211 or the like may perform loop processing of performing step S11 after the processing of step S13.

In this way, in the diagnostic support system 10, first, the provisional information is output by the first recognizer (first learned model 61). By directly inputting RAW data (original image 52) obtained by A/D converting an analog signal from the image sensor 141 to the first recognizer, a detection time delay is shortened, and real-time property of inspection is improved. Next, the confirmation information is output by the second recognizer (second learned model 62). By inputting the preprocessed image to the second recognizer having high recognition accuracy, it is possible to enhance recognition accuracy and improve reliability.

Second Embodiment

Figure 10:
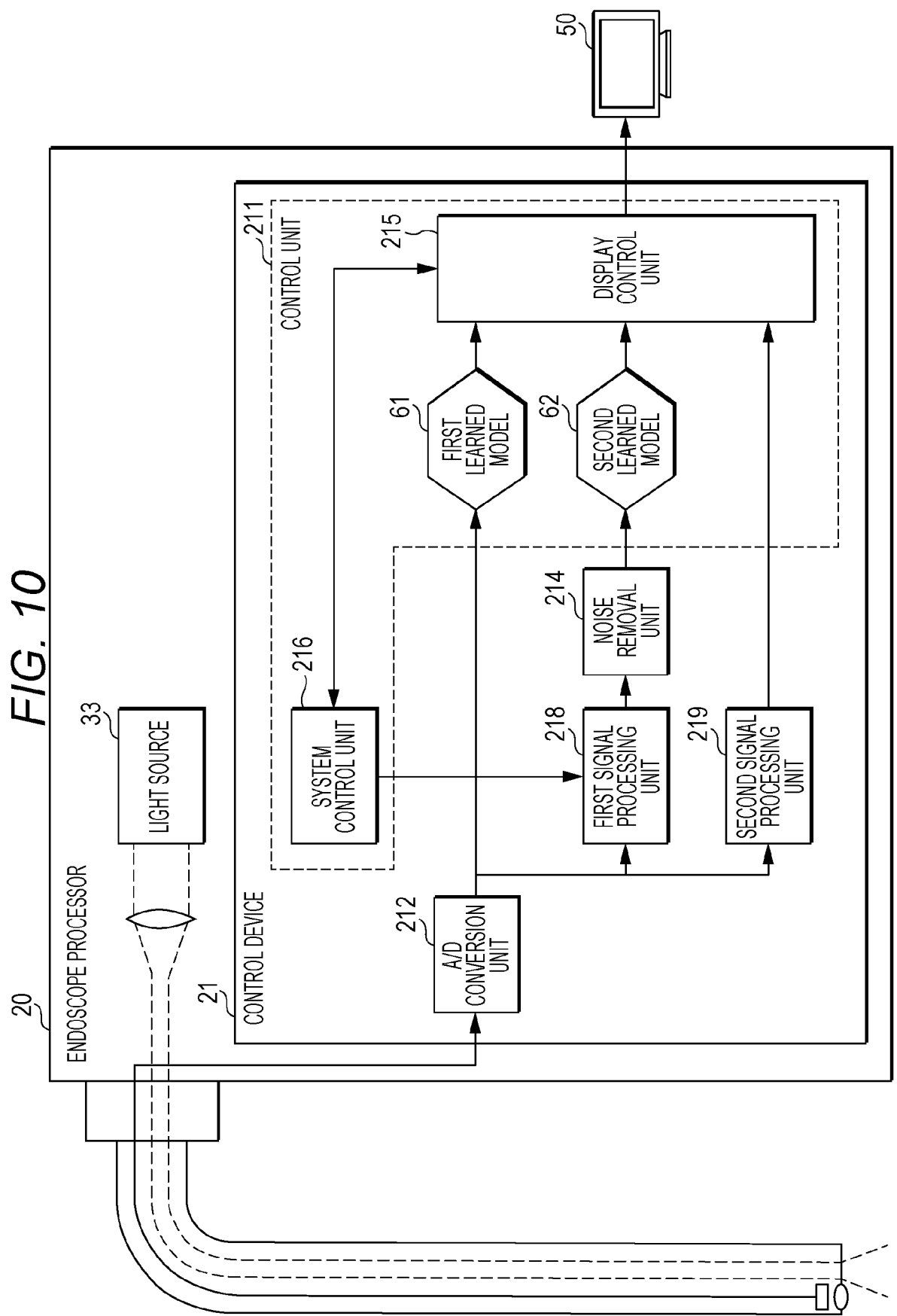
FIG. 10 is a functional block diagram illustrating a configuration of a control device in a second embodiment.

In the second embodiment, the light quantity control information based on the light quantity information is output to the first signal processing unit instead of the light source 33 of the endoscope processor 20. FIG. 10 is a functional block diagram illustrating a configuration of a control device 21 according to the second embodiment. Since the configuration of the diagnostic support system 10 in the second embodiment is similar to the configuration in the first embodiment except that the control device 21 is provided with a first signal processing unit 218 and a second signal processing unit 219, and the details of the processing executed by the diagnostic support system 10 are different, the same reference numerals are given to the common configurations and the detailed description thereof is omitted.

In the second embodiment, the system control unit 216 acquires light quantity information output from the display control unit 215, reads a light quantity control information database (not illustrated) stored in advance, and acquires light quantity control information including information of a parameter suitable for image processing of the original image 52. The system control unit 216 outputs the light quantity control information to the first signal processing unit 218. In the second embodiment, the image processing is performed on the original image 52 instead of the light quantity control of the light source 33 of the first embodiment on the basis of the brightness of the original image 52, whereby the brightness of the lesion section included in the processed image 54 input to the second learned model 62 is adjusted to improve the image recognition accuracy. That is, the light quantity control information in the second embodiment includes information related to parameter control of a signal processing circuit according to the brightness of the image.

The first signal processing unit 218 is a signal processing circuit that performs various types of image processing such as enlargement/reduction of the original image 52 and change of the number of bits using ASIC or the like. Further, the first signal processing unit 218 changes parameters of various signal processing on the basis of the light quantity control information output from the system control unit 216, and performs image processing for appropriately adjusting the brightness of the original image 52. The first signal processing unit 218 inputs an image subjected to image processing for enhancing lesion recognition accuracy to the noise removal unit 214.

The second signal processing unit 219 is a signal processing circuit that performs various types of image processing such as gamma correction and contour enhancement of the original image 52 using ASIC or the like. The second signal processing unit 219 generates an image (endoscope image 53) subjected to image processing for making it easy for the user to view the image, and inputs the image to the display control unit 215.

Figure 11:
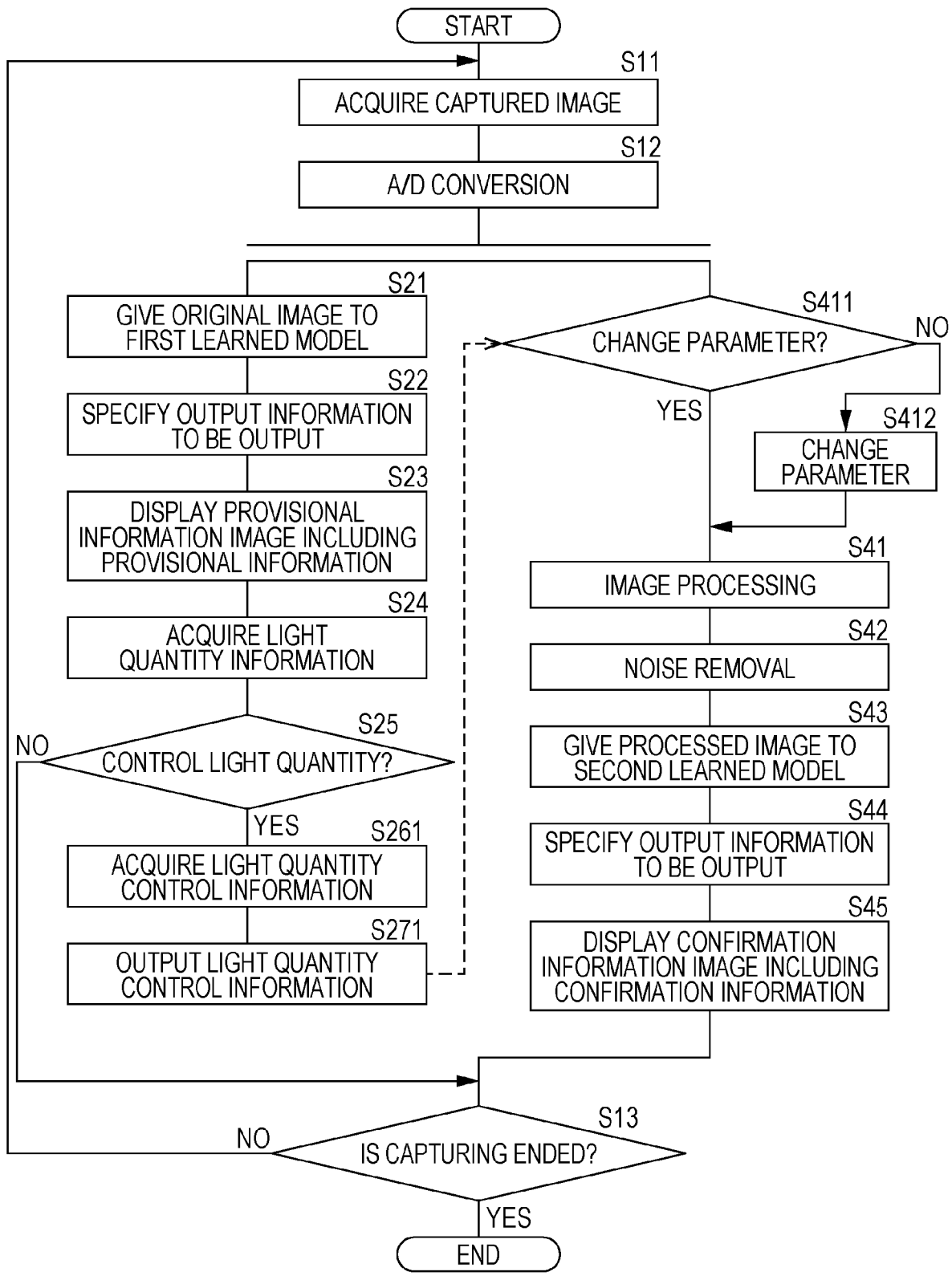
FIG. 11 is a flowchart illustrating an example of a processing procedure executed by a diagnostic support system of the second embodiment.

FIG. 11 is a flowchart illustrating an example of a processing procedure executed by the diagnostic support system 10 of the second embodiment. The flowchart illustrated in FIG. 11 describes processing executed by the control unit 211, the A/D conversion unit 212, the first signal processing unit 218, the second signal processing unit 219, and the noise removal unit 214 of the endoscope processor 20. The processing common to those in FIG. 9 of the first embodiment are denoted by the same step numbers, and a detailed description thereof will be omitted.

The A/D conversion unit 212 acquires the captured image 51 from the endoscope 40 (step S11), performs A/D conversion on the acquired captured image 51 (step S12), and generates the original image 52. The control unit 211 gives the original image 52 to the first learned model 61 (step S21), and specifies output information to be output (step S22). The control unit 211 temporarily stores provisional information based on the specified output information in the auxiliary memory device 23. The control unit 211 generates the provisional information image 55 in which the provisional information is superimposed and displayed on the endoscope image 53, and displays the provisional information image 55 including the provisional information on the display device 50 (step S23).

The control unit 211 acquires light quantity information regarding brightness of the image of the captured region including the lesion section of the original image 52 (step S24). The control unit 211 determines whether or not to control the light quantity of the original image 52 on the basis of the light quantity information (step S25). For example, in a case where the brightness of the captured region including the lesion section of the original image 52 is within a range of a preset threshold value, it is determined that the light quantity control is unnecessary because the brightness of the lesion section is appropriate. If it is determined that the light quantity control is unnecessary (step S25: NO), the control unit 211 skips the processing of the light quantity control and proceeds to step S13.

On the other hand, in a case where the brightness of the captured region including the lesion section of the original image 52 is equal to or higher than a preset threshold value or equal to or lower than a preset threshold value, it is determined that the light quantity control is necessary because the lesion section is too bright or too dark. If it is determined that the light quantity control is necessary (step S25: YES), the control unit 211 refers to a light quantity control information database stored in advance and acquires light quantity control information according to the light quantity information (step S261). The control unit 211 outputs the acquired light quantity control information to the first signal processing unit 218 (step S271).

The control unit 211 or the like generates a sub-process and performs the processing of step S411 in parallel with the processing of step S21 and subsequent steps. The control unit 211 or the like may synchronize processing by performing inter-process communication in these two processes. The first signal processing unit 218 acquires the light quantity control information output from the control unit 211, and determines whether or not to change the parameter of the signal processing circuit (step S411). If it is determined that the parameter change is unnecessary (step S411: YES), the first signal processing unit 218 skips the parameter change processing and advances the processing to the next step S41.

On the other hand, if it is determined that the parameter change is necessary (step S411: NO), the first signal processing unit 218 changes the parameter of the signal processing circuit on the basis of the light quantity control information (step S412), and performs various types of image processing on the original image 52 according to the changed parameter (step S41). The noise removal unit 214 performs noise removal on the image subjected to the image processing (step S42), and generates the processed image 54. The captured region including the lesion section of the processed image 54 is adjusted to appropriate brightness.

The control unit 211 gives the processed image 54 to the second learned model 62 (step S43), and specifies output information to be output (step S44). The control unit 211 temporarily stores confirmation information based on the specified output information in the auxiliary memory device 23. The control unit 211 generates a confirmation information image 56 in which the confirmation information is superimposed and displayed on the endoscope image 53, and displays the confirmation information image 56 including the confirmation information on the display device 50 (step S45).

The control unit 211 determines whether or not the capturing has ended (step S13). If it is determined that the capturing has not been ended (step S13: NO), the control unit 211 returns the processing to step S11 and acquires a new captured image. If it is determined that the capturing has been ended (step S13: YES), the control unit 211 or the like ends a series of processing.

According to the present embodiment, by performing parameter control of the signal processing circuit using the output signal of the first recognizer, an image subjected to more appropriate preprocessing is input to the second recognizer. It is possible to enhance the recognition accuracy in the second recognizer without controlling the light source 33.

Third Embodiment

In the third embodiment, the contents of the noise removal unit 214 and the second learned model 62 are different, and the noise removal is performed in the second learned model 62. Since the configuration of the diagnostic support system 10 in the second embodiment is similar to the configuration in the first embodiment and the second embodiment except that the contents of the noise removal unit 214 and the second learned model 62 are different, the common configuration is denoted by the same reference numeral, and the detailed description thereof is omitted.

The noise removal unit 214 according to the third embodiment holds images of immediately preceding and further immediately preceding frames of noise removal. The noise removal unit 214 inputs the frame image, the immediately preceding frame image, and the further immediately preceding frame image that are held to the second learned model 62 without performing image processing related to noise removal.

Figure 12:
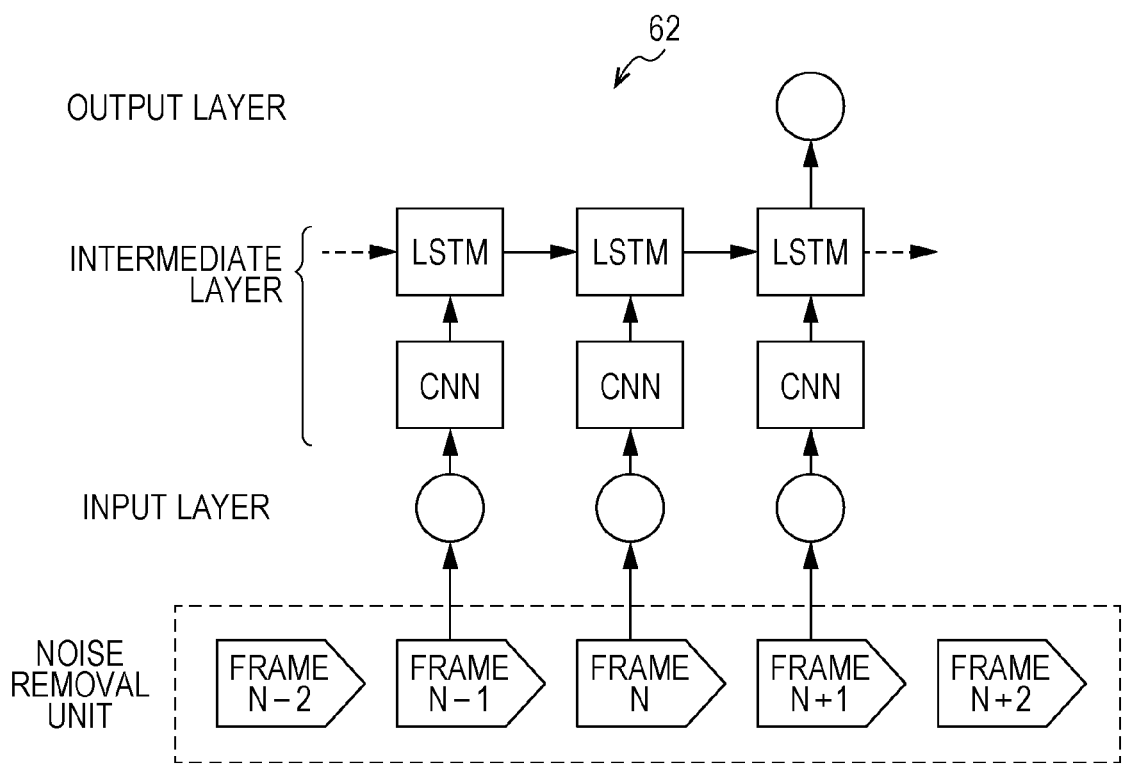
FIG. 12 is an explanatory diagram regarding a second learned model in a third embodiment.

FIG. 12 is an explanatory diagram relating the second learned model 62 in the third embodiment. The control unit 211 performs learning on the basis of training data associated with the identification result of the presence or absence and the contents of the lesion in a plurality of time-series endoscope images from which noise has not been removed and the last endoscope image in the time series from which noise has been removed, thereby constructing (generating) a neural network that inputs the plurality of time-series endoscope images and outputs the identification result of the presence or absence and content of the lesion in the last endoscope image in the time-series from which noise has been removed.

An input layer has a single or a plurality of neurons that receive a plurality of endoscope images in time series, and passes the plurality of input endoscope images to an intermediate layer. The intermediate layer has a multilayer structure in which an autoregressive layer is connected after a convolution layer and a pooling layer of CNN. The autoregressive layer is implemented as, for example, a long short term memory (LSTM) model, and a neural network including such an autoregressive layer is referred to as a recurrent neural network (RNN). The feature amount of each of the endoscope images input in time series is extracted by the convolution layer and the pooling layer. The autoregressive layer outputs a change amount in each of the extracted feature amounts. The output layer includes one or a plurality of neurons, and generates and outputs an identification result of the presence or absence and content of the lesion in the last endoscope image in time series on which noise removal has been performed on the basis of the change amount in the feature amount of each endoscope image output from the intermediate layer. Learning for the neural network forming a connection structure with the CNN and the RNN is performed, for example, by combining backpropagation and backpropagation through time (BPTT). Note that the configuration of the second learned model 62 illustrated in FIG. 12 is an example, and the present embodiment is not limited thereto.

The noise removed by the learned model 237 includes various noises. A first example of the noise is noise such as so-called noise included in the captured image 51 obtained from the image sensor. A second example of the noise is a foreign substance such as bubbles included in the processed image 54. For example, in a case where the bubbles are included in the processed image 54, since the shape thereof is similar to that of the lesion section, there is a possibility that the bubbles are erroneously identified as the lesion section. Unlike the lesion section, these foreign substances cause changes such as movement and disappearance.

According to the present embodiment, the second recognizer recognizes information related to a lesion section including information related to noise. Since the learned model 237 also performs noise removal, the recognition accuracy can be further improved.

Fourth Embodiment

Figure 13:
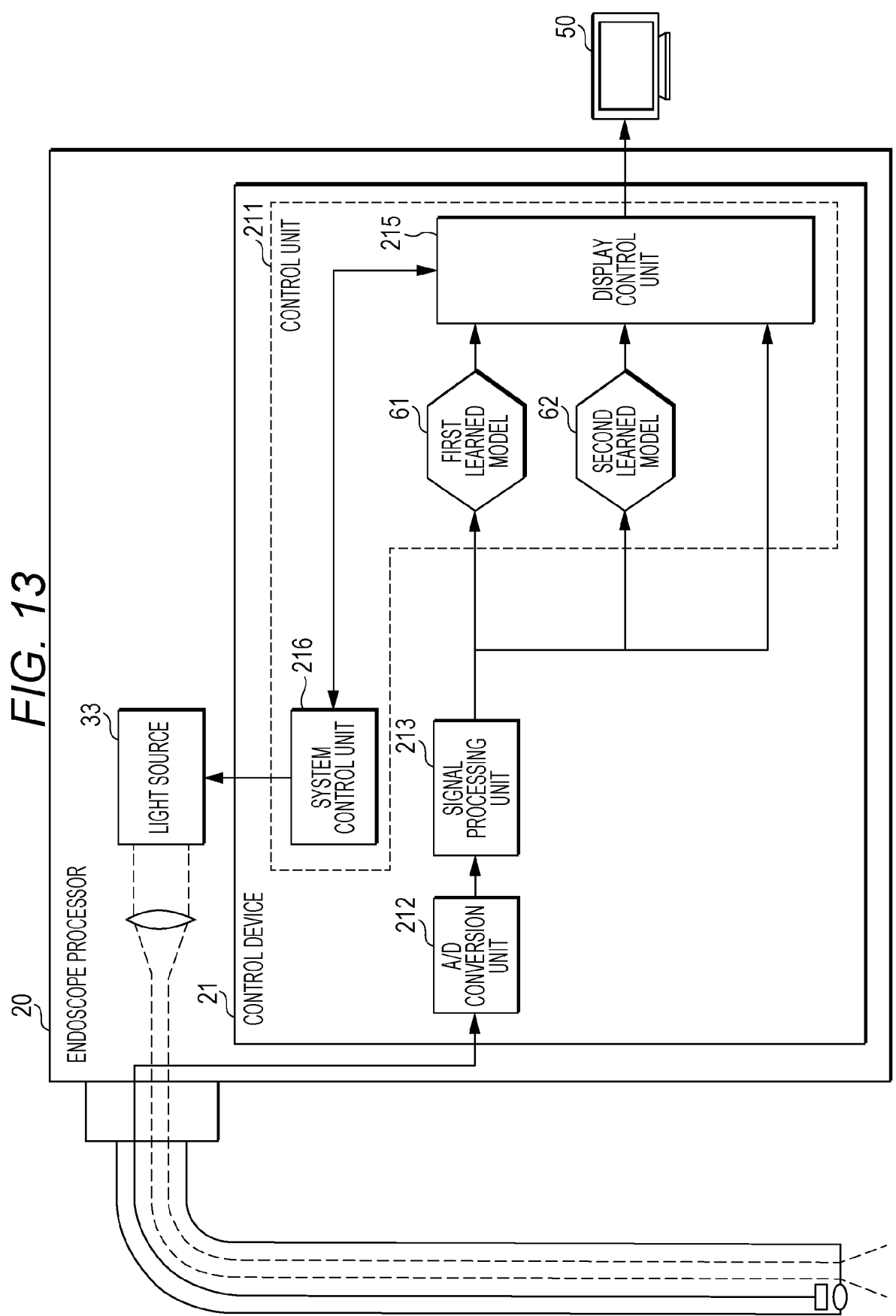
FIG. 13 is a functional block diagram illustrating a configuration of a control device in a fourth embodiment.

In the fourth embodiment, images subjected to the same image processing are input to the first learned model 61 and the second learned model 62. FIG. 13 is a functional block diagram illustrating a configuration of a control device 21 according to the fourth embodiment. Since the configuration of the diagnostic support system 10 in the fourth embodiment is similar to the configuration in the first embodiment except that details of processing executed by the diagnostic support system 10 are different, the same reference numerals are given to common configurations, and a detailed description thereof will be omitted.

As illustrated in FIG. 13, in the third embodiment, the captured image 51 is A/D-converted by the A/D conversion unit 212, and various types of image processing such as gamma correction, contour enhancement, and enlargement/reduction are performed by the signal processing unit 213. The images subjected to various types of image processing are input to the first learned model 61 and the second learned model 62, respectively. Note that the image input to each of the first learned model 61 and the second learned model 62 may be further subjected to image processing such as noise removal by a noise removal unit (not illustrated) after the image processing by the signal processing unit 213.

The first learned model 61 and the second learned model 62 are learned models having different numbers of layers. The image information subjected to the same preprocessing is input to the first learned model 61 and the second learned model 62. The second learned model 62 has a configuration in which the number of intermediate layers is larger than that of the first learned model 61 and the recognition accuracy is high. As in the first embodiment and the second embodiment, the provisional information in which the presence or absence of the lesion section is recognized is output from the first learned model 61. The confirmation information in which the presence or absence and content of the lesion section are recognized is output from the second learned model 62.

In the fourth embodiment, as in the first embodiment, the control unit 211 of the endoscope processor 20 outputs light quantity control information to the light source 33 on the basis of light quantity information of the image output from the first learned model 61. The light quantity of the light source 33 is controlled by the light quantity control information. The first learned model 61 and the second learned model 62 are input with images obtained by adjusting and capturing the captured region including the lesion section to have appropriate brightness. Note that, similarly to the second embodiment, the control unit 211 may output light quantity control information to the signal processing unit 213 to adjust the brightness of the image.

Fifth Embodiment

The fifth embodiment is different from the first embodiment in a notification mode of the provisional information and the confirmation information. Since the hardware configuration of the diagnostic support system 10 in the fifth embodiment is similar to that in the first embodiment, the same reference numerals are given to common configurations, and the detailed description thereof will be omitted.

Figure 14:
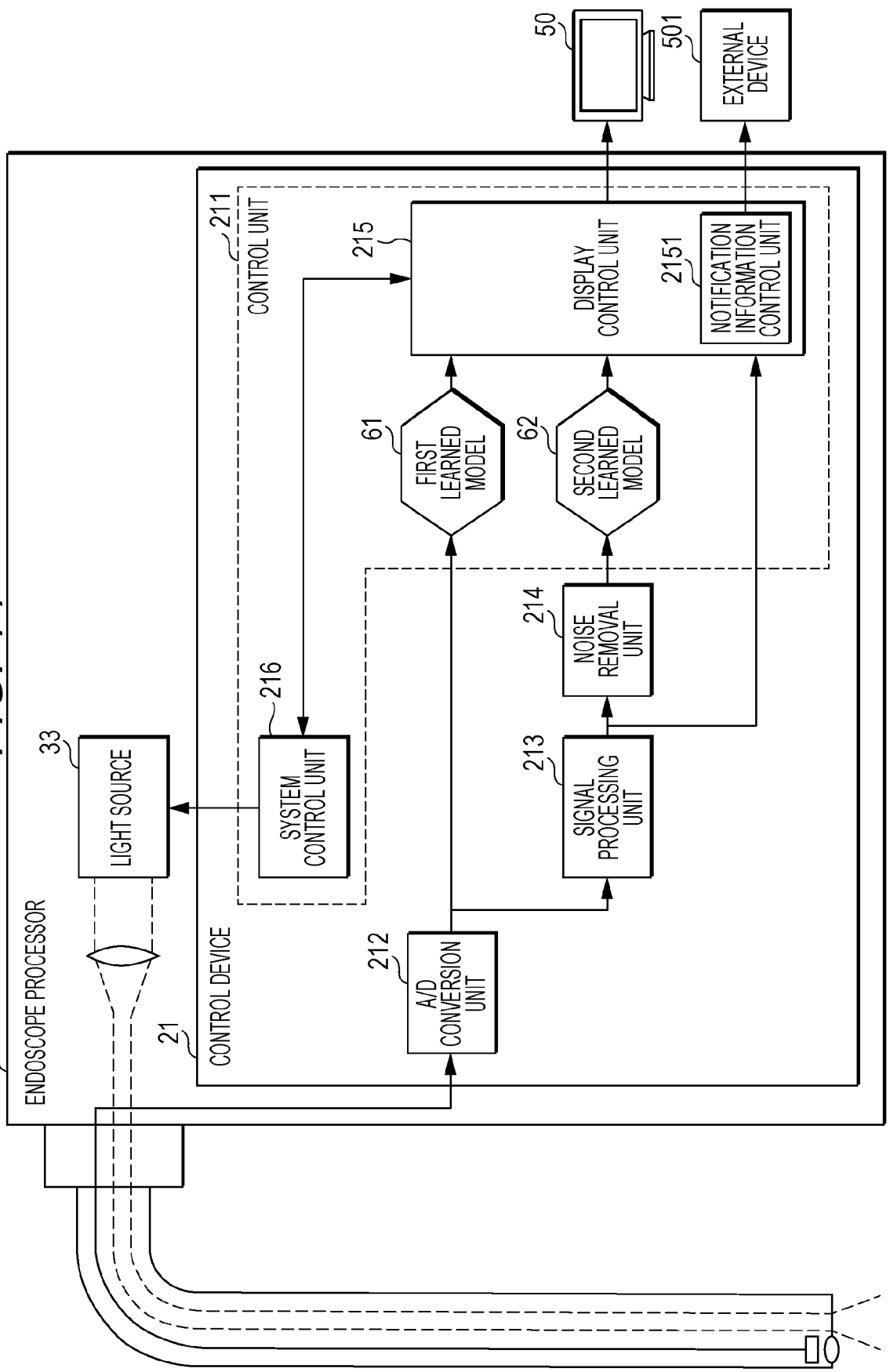
FIG. 14 is a functional block diagram illustrating a configuration of a control device in a fifth embodiment.

FIG. 14 is a functional block diagram illustrating a configuration of a control device 21 according to the fifth embodiment. The control unit 211 of the diagnostic support system 10 in the fifth embodiment realizes a function of a notification information control unit 2151 by executing the program 63 stored in the auxiliary memory device 23.

The provisional information and the confirmation information are not limited to those output together with the image using the marker or the like, and may be output by, for example, synthesized speech, beep sound, music, vibration, or the like. The notification information control unit 2151 generates provisional notification information including the provisional information and confirmation notification information including the confirmation information according to the provisional information based on the output information from the first learned model 61 and the confirmation information based on the output information from the second learned model 62 acquired by the display control unit 215.

In this case, the notification information control unit 2151 generates the provisional notification information and the confirmation notification information in different notification modes so that the provisional information and the confirmation information can be distinguished in the notification subject by using different beep sounds, music, synthesized speech, vibration patterns, and the like. For example, the notification information control unit 2151 provides notification of the provisional notification information using a first beep sound, and notifies the user of the confirmation notification information using a second beep sound different from the first beep sound. The notification information control unit 2151 may change the combination of the sound pattern and the vibration pattern to provide notification of the provisional notification information and the confirmation notification information in a distinguishable manner. When the provisional information and the confirmation information do not match as in, for example, a case where the absence of the lesion is output as the provisional information and then the presence of the lesion is output as the confirmation information, the notification information control unit 2151 may notify the user in a distinguishable manner using a further different notification mode such as a third beep sound. When the presence of the lesion is output as the provisional information and then the absence of the lesion is output as the confirmation information, the notification information control unit 2151 may notify the user in a distinguishable manner using a notification mode such as a fourth beep sound indicating that the presence of the lesion has been canceled as the confirmation notification information. The notification information control unit 2151 refers to a table that stores the provisional information, the confirmation information, and the notification pattern in association with each other, and generates the provisional notification information and the confirmation notification information.

The notification information control unit 2151 outputs the generated provisional notification information and confirmation notification information to the user via the external device 501. The external device 501 includes, for example, a speaker provided in the endoscope processor 20, a vibration generator provided in the endoscope 40, and the like. The external device 501 may include, for example, a speaker, a vibration generator, and the like included in a smartphone worn by the user of the endoscope 40. Under the control of the display control unit 215, the notification information control unit 2151 outputs the provisional notification information and the confirmation notification information regarding the frame of the endoscope image 53 from the external device 501 in association with a time point at which the frame of the endoscope image 53 in which the lesion is confirmed is displayed. That is, the user can confirm the lesion section in the endoscope image 53 displayed on the display device 50 and the provisional notification information and the confirmation notification information for the lesion section in association with each other. Note that timings at which the provisional notification information and the confirmation notification information are output are not limited to those controlled by the display control unit 215, and may be those controlled by the notification information control unit 2151.

According to the present embodiment, it is possible to improve the visibility of the endoscope image 53 by notifying the user such as a doctor using the speaker, the vibration generator, or the like, which is another notification means, without superimposing the notification information on the endoscope image 53.

Note that the embodiments disclosed as described above should be considered exemplary in all respects and not restrictive. The technical features described in the examples can be combined with each other, and the scope of the present invention is intended to include all modifications within the scope of the claims and the scope equivalent to the claims.

REFERENCE SIGNS LIST 10 diagnostic support system
20 endoscope processor
21 control device
211 control unit
212 A/D conversion unit
213 signal processing unit
214 noise removal unit
215 display control unit
2151 notification information control unit
218 first signal processing unit
219 second signal processing unit
22 main memory device
23 auxiliary memory device
33 light source
40 endoscope
50 display device
501 external device
51 captured image
52 original image
53 endoscope image
54 processed image
55 provisional information image
56 confirmation information image
61 first learned model
62 second learned model
63 program
141 image sensor

The invention claimed is:

1. An endoscope comprising:
   an insertion portion having a bending portion, a distal tip connected to the bending portion, and an image sensor provided at the distal tip;
   a user-operated operation unit connected to an end of the insertion portion opposite from the distal tip;
   a housing housing a processor and a light source;
   a light guide tube connecting the operation unit and the housing, and configured to guide light from the light source to the insertion portion via the operation unit, and to transmit image data from the image sensor to the processor in the housing; and
   a display connected to the processor and configured to display images processed by the processor, wherein the processor
      acquires an image captured by the image sensor from the image data generated by the image sensor and transmitted to the processor,
      recognizes a lesion section from the acquired image with a first recognition accuracy, and
      recognizes the lesion section from the acquired image with a second recognition accuracy higher than the first recognition accuracy,
      acquires provisional information including a recognition result recognized by the processor with the first recognition accuracy,
      outputs a first image including the acquired provisional information to the display,
      acquires confirmation information for the provisional information including a recognition result recognized by the processor with the second recognition accuracy, and
      outputs a second image including the acquired confirmation information to the display,
   wherein the confirmation information is output later than the provisional information.

2. The endoscope according to claim 1, wherein the processor erases the provisional information is erased from the image that includes the provisional information in response to the confirmation information being different from the provisional information.

3. The endoscope according to claim 1, wherein the image is converted by a converter that converts an electric signal representing the image data obtained from the image sensor of the endoscope into RAW data, and the RAW data converted image is input to the processor.

4. The endoscope according to claim 1, wherein the image is processed by
   a converter that converts an electric signal representing the image data obtained from the image sensor of the endoscope into RAW data,
   a signal processing circuit, and
   a noise removal unit and
the processed image is input to the processor.

5. The endoscope according to claim 1, wherein
   the image is an image of a captured region of the lesion section,
   light quantity information of the brightness of a captured region of the lesion section of the image that includes the lesion section recognized by the processor is acquired, and
   the image is subjected to predetermined processing according to the acquired light quantity information and the processed image is input to the processor.

6. The endoscope according to claim 5, wherein the processor controls the light source in response to the light quantity information of the brightness of the captured region of the lesion section.

7. The endoscope according to claim 5, wherein the predetermined processing includes at least any one of parameter control, y correction, contour enhancement, and noise removal of a signal processing circuit.

* * * * *